United States Patent
Bleich et al.

(12)

(10) Patent No.: US 6,469,063 B1
(45) Date of Patent: Oct. 22, 2002

(54) INHIBITION OF INFLAMMATION VIA INHIBITION OF COX-2 GENE TRANSCRIPTION

(75) Inventors: David Bleich, Pasadena; Songyuan Chen; Xiao Han, both of Duarte, all of CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/714,889

(22) Filed: Nov. 17, 2000

Related U.S. Application Data (60) Provisional application No. 60/166,161, filed on Nov. 18, 1999.

(51) Int. Cl.[7] .............................................. A61K 31/216
(52) U.S. Cl. ......................................... 514/538; 514/540
(58) Field of Search .................................. 514/540, 538

(56) References Cited

PUBLICATIONS

Michaluart et al., Cancer Research, 59/10, (2347–2352) (May 15, 1999) (abstract).*
Gierse, James K. et al., Kinetic Basis for Selective Inhibition of Cyclo–oxygenases, *Biochem. J.*(1999) 339: 607–614.
Kirchner, T. et al., Evaluation of the Antiinflammatory Activity of a Dual Cyclooxygenase–2 Selective/5–Lipoxygenase Inhibitor, RWJ 63556, in a Canine Model of Inflammation, *The Journal of Pharmacology and Experimental Therapeutics* (1997) 282:1094–1101.
Chan, C.C. et al., Rofecoxib [Vioxx, MK–0966; 4(4'–Methylsulfonylphenyl)–3–phenyl–2(5H)–furanone]: A Potent and Orally Active Cyclooxygenase–2 Inhibotor. Pharmacological and Biochemical Profiles, *The Journal of Pharmacology and Experimental Therapeutics* (1999) 290:551–560.
Callejas, Nuria A. et al., Inhibition of Prostaglandin Synthesis Up–Regulates Cyclooxygenase–2 Induced by Lipopolysaccharide and Peroxisomal Proliferators, *The Journal of Pharmacology and Experimental Therapeutics* (1999) 288: 1235–1241.
Cho, Hidetsura et al., Novel Caffeic Acid Derivatives: Extremely Potent Inhibitors of 12–Lipoxygenase, *J. Med. Chem.* (1991) 34:1503–1505.

* cited by examiner

*Primary Examiner*—Phyllis G. Spivack
(74) *Attorney, Agent, or Firm*—Rothwell, Figg, Ernst & Manbeck (57) ABSTRACT

The present invention is directed to a method of treating inflammation comprising administering to a subject in need thereof an amount of a caffeic acid derivative sufficient to inhibit the transcription of COX-2. In a preferred embodiment the caffeic acid derivative is a cyanocinnamate, most preferably cinnamamyl-3,4-dihydroxy-α-cyanocinnamate.

5 Claims, 9 Drawing Sheets

INHIBITION OF INFLAMMATION VIA INHIBITION OF COX-2 GENE TRANSCRIPTION

CROSS-REFERENCE TO RELATED APPLICATIONS

This application is related to provisional application No.60/166,161, filed Nov. 18, 1999, the specification of which is incorporated herein by reference.

TECHNICAL FIELD

The present invention relates to methods for the treatment of inflammation, inhibition of cyclooxygenase-2 gene transcription, and in vivo activities of caffeic acid derivatives.

BACKGROUND OF THE INVENTION

Unlike cyclooxygenase-1 (COX-1), an enzyme that has constitutive expression in many tissues, cyclooxygenase-2 (COX-2) is induced by inflammatory stimuli like cytokines [1], lipopolysaccharide [2, 3], and mitogens [4, 5]. Both enzymes convert arachidonic acid to prostaglandin E2 (PGE2) and show similar kinetics for converting arachidonic acid to prostaglandin G2 and prostaglandin H2[6], but each appears to have different selectivity for non-steroidal anti-inflammatory agents. With the recent development of specific COX-2 inhibitors, investigators have been able to more precisely define the roles of COX-1 and COX-2 enzymes in biological systems.

Cytokine-mediated COX-2 gene activation in pancreatic β-cells inhibits glucose stimulated insulin secretion through the generation of PGE2. The role of COX-2 gene activation and PGE2 production in the context of cellular stress may be viewed from two perspectives. First, PGE2 production is an attempt by the pancreatic β-cells to preserve function during an immune inflammatory attack. By generating PGE2, the β-cell sets off a regulatory mechanism to limit glucose stimulated insulin secretion that in turn allows the β-cell to conserve ATP and utilize its energy stores to transcribe genes that confer protection against oxidative stress. In addition, PGE2 release from β-cells may bias the immune towards a Th2 profile. PGE2 stimulates Th2 cytokine production in human lymphocytes [15], inhibits LPS-induced IL-1β production in microglial cells [3], limits Th1 cytokine responses [16], and prevents generation of interferon-γ by inhibiting human IL-12 production [17]. Alternatively, PGE2 acts as a proinflammatory agent by inducing leukocyte migration [18], endothelial adhesion [19], painful response [20], and antigen stimulated interferon-γ production in Th1 lymphocytes [21]. These apparent conflicting actions of PGE2 may ultimately be related to the ambient concentration of PGE2 in the affected tissue. Low concentrations of PGE2 as seen during basal states may promote cell survival, while high concentrations of PGE2 may promote cell demise. In this context, it is interesting to note that both COX-1 and COX-2 have endogenous peroxidase activity that may also contribute to either a pro- or anti-inflammatory state [6].

Pancreatic islets, like other tissues, express low basal levels of COX-2 and its metabolic end product, PGE2. Cellular stress can increase COX-2 mRNA levels from 3 to 5-fold and PGE2 production by greater than 100-fold. Early studies demonstrated that PGE2 production could be stimulated with alpha-adrenergic agonists and that prostaglandin synthase inhibitors could reverse the alpha-adrenergic-mediated inhibition of glucose-stimulated insulin secretion in human subjects [22]. Further work revealed that PGE2 had no effect as an insulin secretagogue, but did inhibit glucose-stimulated insulin secretion in pancreatic β-cells [8, 9]. PGE2 mediates its inhibitory effect on glucose-stimulated insulin secretion through stimulation of a pertussis-toxin sensitive GTPase protein that has yet to be cloned, but is likely to reside in the insulin secretory granule [23].

These findings led to the hypothesis that PGE2 may mediate the inhibitory effect of interleukin-1β (IL-1β) on glucose-stimulated insulin secretion, since IL-1β, itself, increases PGE2 production. However, McDaniel and colleagues demonstrated that nitric oxide (NO), not PGE2, mediates the inhibitory effects of IL-L1β on glucose-stimulated insulin secretion in rat pancreatic islets [24]. In addition, Turk and colleagues showed that L-NMMA, an inhibitor of iNOS, abrogated the inhibitory effect of IL-1β on glucose stimulated insulin secretion and partially inhibited PGE2 production through a mechanism that is likely to be post-translational (i.e., NO increases arachidonic acid substrate availability by inhibiting the reacylation of arachidonic acid into membrane phospholipid [25]). Thus, NO led to higher intracellular levels of arachidonic acid that could be converted to 12-HETE by 12-LO, and theoretically, PGE2 by COX-2, since arachidonic acid is a substrate for both 12-LO and COX-2. These results support prior studies in human islets showing that indomethacin, a non-selective cyclooxygenase inhibitor, enhanced glucose stimulated insulin secretion [26]. By increasing ambient arachidonic acid levels in the β-cell, indomethacin enhanced glucose stimulated insulin secretion since arachidonic acid, itself, is a potent insulin secretagogue [27]. In addition, by blocking PGE2 production through the inactivation of COX-1 and COX-2, indomethacin prevented PGE2 mediated inhibition of glucose stimulated insulin secretion.

More recently, Robertson demonstrated that the selective COX-2 inhibitor NS-398 partially restored glucose-stimulated insulin secretion in HIT cells treated with IL-1β for 24 hours (Diabetes 1999; 48:Supp. 1 :A1017). The implication of this study is that PGE2 may participate in cytokine-mediated pancreatic β-cell dysfunction, although this hypothesis has yet to be formally proven.

The selective COX-2 inhibitors discovered to date work at the post-transcriptional level. Callejas, et al. (1999) [30], for example, reported that indomethicin and the COX-2 specific inhibitor NS398, while both suppressing the activity of COX-2, lead to an accumulation of the protein in primary cultures of fetal hepatocytes and in cultured peritoneal macrophages. The authors found that the increased COX-2 levels were not the result of increased mRNA production, postulating that the accumulation was due to post-translation effects, such as increased stabilization of the enzyme, or decrease in the synthesis of prostaglandins that favor COX-2 degradation, or both. Callejas, et al. at 1240. Chan, et al. (1999) [31] obtained similar results with the selective COX-2 inhibitor rofecoxib in human osteosarcoma cells and Chinese hamster ovary cells. Chan, et al. found their results to be consistent with a two-step time-dependant model of reversible enzyme inhibition involving the formation of a tightly bound 1:1 enzyme-inhibitor complex. Chan, et al. at 555, 557. Gierse, et al. (1999) [32] conducted an in vitro comparison of the selective COX-2 inhibitor celecoxib and several non-steroidal anti-inflammatory drugs (NSAIDs), and proposed at least four distinct mechanisms of COX-2 inhibition, all of them at the post-translational level: (i) competitive; (ii) tight binding, time-dependent; (iii) weak binding, mixed; and (iv) covalent binding. Gierse, et al. at 615. In a recent minireview of research on the mechanisms of COX-1 and COX-2 catalysis and inhibition, Marnett, et al. (1999) [33] acknowledged that the regulatory aspects of cyclooxygenase function where poorly-understood (for example, the reason for the existence of two distinct cyclooxygenase genes—COX-1 and COX-2—sometimes expressed in the same cell type, is not known). Marnett, et al. at 22906. The authors described the topic as "an extremely important and exciting area of investigation." Id. Furthermore, Michaluart et al. [35] investigated the effect of caffeic acid phenethyl ester (CAPE) on COX-2 activity and expression. Using both in vitro and in vivo models they demonstrated that this caffeic acid derivative inhibited the enzyme activity of both COX-1 and COX-2 at low concentration (14–28 $\mu$M), while higher concentrations (35–70 $\mu$M) inhibited COX-2 gene transcription. In addition, they utilized the rat carrageenan air pouch model (a standard model for evaluating anti-inflammatory properties of various drugs) to demonstrate that CAPE inhibited prostaglandin synthesis in a dose-dependent fashion (10–100 mg/kg).

Kirchner, et al. [36] utilized a dual COX-2/5-lipoxygenase inhibitor (RWJ63556) to inhibit a localized inflammatory response in a canine model. Oral administration of RWJ63556 at a dose of 3 mg/kg lead to significant sustained inhibition of leukocyte influx and prostaglandin synthesis over a 24 hour period, and compared to other COX-1/COX-2 inhibitors like dexamethasone and indomethacin.

Pancreatic $\beta$-cells express low levels of COX-1 mRNA and somewhat higher levels of COX-2 mRNA when cytokines are not present [7]. Upon stimulation with cytokines like IL-1$\beta$, COX-2 mRNA increases several fold, while COX-1 mRNA expression remains unchanged. Prior studies demonstrated that PGE2, the metabolic end product of cyclooxygenase activity, inhibits glucose-stimulated insulin secretion in rat islets [8, 9] and these observations led to the hypothesis that cytokine-induced pancreatic $\beta$-cell cytotoxicity may be, in part, due to excessive PGE2 production.

It has been demonstrated recently that 12-lipoxygenase (12-LO) knockout mice are resistant to streptozotocin-induced diabetes [10] and leading to the hypothesis that part of this cytoprotective effect resided in the pancreatic $\beta$-cell, since 12-LO is preferentially expressed in $\beta$-cells compared to $\alpha$- and $\beta$-cells [11]. Moreover, 12-LO knockout mice demonstrated no cytokine-inducible conversion of arachidonic acid to 12-hydroxyeicosatetraenoic acid (12-HETE) as expected, implying that 12-HETE generation may be cytotoxic to pancreatic $\beta$-cells. Prior studies have demonstrated that arachidonic acid microparticles could induce COX-2 gene expression [12], raising the possibility that the 12-LO pathway product 12-HETE might also affect COX-2.

Certain caffeic acid derivatives have been found to be potent inhibitors of 12-LO. Cho, et al. (1991) [34]. This lipoxygenase is know to be implicated in inflammation and atherosclerosis through its production of the arachidonic acid metabolite 12-HETE. However, in vitro studies specifically showed that these derivatives did not inhibit cyclooxygenase activity. Cho, et al. at 1505.

It has now been found that lipoxygenase inhibitors do, in fact inhibit COX-2 activity, but by acting at the transcriptional level and suppressing expression of the COX-2 gene.

SUMMARY OF THE INVENTION

The present invention relates to methods of treating inflammation comprising administering a COX-2 transcription-inhibiting amount of a caffeic acid derivative, preferably a cyanocinnamate. In a preferred embodiment, cinnamamyl-3,4-dihydroxy-$\alpha$-cyanocinnamate is used. It has been found that this class of compounds, known in the art as 12-lipoxygenase inhibitors, have potent in vivo COX-2 inhibiting effect, unlike other classes of lipoxygenase inhibitors. The inhibitory effect of the caffeic acid derivatives on COX-2 is believed to occur at the transcriptional level, which may be one explanation for why the effect was not observed in in vitro enzyme assays such as those reported by Cho, et al. [34]

The COX-2 gene and 12-lipoxygenase (12-LO) gene are preferentially expressed over other isoforms of cyclooxygenase and lipoxygenase in pancreatic $\beta$-cells. Inhibition of either COX-2 or 12-LO can prevent cytokine-induced pancreatic $\beta$-cell dysfunction as determined by glucose-stimulated insulin secretion. It has been found that 12-HETE significantly increases COX-2 gene expression and prostaglandin E2 production, while a closely related lipid 15-hydroxyeicosatetraenoic acid (15-HETE), does not. However, interleukin-1$\beta$ stimulated prostaglandin E2 production is completely inhibited by the preferential lipoxygenase inhibitor cinnamamyl-3,4-dihydroxy-$\alpha$-cyanocinnamate (CDC), a caffeic acid derivative. Finally, IL-1$\beta$ has been found to fail to stimulate prostaglandin E2 production in 12-LO knockout islets, while C57BL/6 islets showed an 8-fold increase.

These data demonstrate not only that 12-HETE mediates cytokine-induced COX-2 gene transcription and prostaglandin E2 production in pancreatic $\beta$-cells, but that caffeic acid derivatives, and in particular cynanocinnamates, can inhibit COX-2 activity by suppressing COX-2 gene expression.

BRIEF DESCRIPTION OF THE FIGURES

FIG. 1: Western immunoblot of COX-2 protein expression in RIN m5F cells. 12-HETE (1–10 nM) shows equipotent COX-2 protein stimulation compared to IL-1$\beta$ (0.3 ng/ml) at 24 hours. Lanes 1 and 2 demonstrate control COX-2 levels. Lanes 3 and 4 show IL-1 $\beta$ stimulation. Lanes 5 and 6 show 12-HETE 1 nM stimulation and lanes 7 and 8 show 12-HETE 10 nM stimulation. Shown is one representative blot that was repeated twice.

FIG. 2: Western immunoblot of cultured intact porcine pancreatic islets. Islets were exposed to the indicated agents for 24 hours prior to protein extraction. IL-1 $\beta$ (0.3 ng/ml) stimulated a 3-fold increase in COX-2 protein that was completely inhibited by CDC (11, M). CDC alone did not appreciably affect basal COX-2 protein levels.

Serum and 12-HETE induced a 3-fold increase in COX-2 mRNA expression, while IL-1 $\beta$ induced a 2-fold increase. Shown is one representative autoradiograph out of two replicate experiments

Serum induced a 2-fold increase in COX-2 mRNA expression, while IL-1 $\beta$ and 15-HETE induced a 1.5-fold increase. Shown is one representative autoradiograph out of two replicate experiments.

FIG. 6: PGE2 production in RIN m5F cells. PGE2 was measured from conditioned culture medium 24 hours after the addition of indicated agents. 12-HETE induced a 10-fold greater increase in PGE2 than 15-HETE. Shown are 3–4 individual experiments per condition.

DETAILED DESCRIPTION

Figure 9:
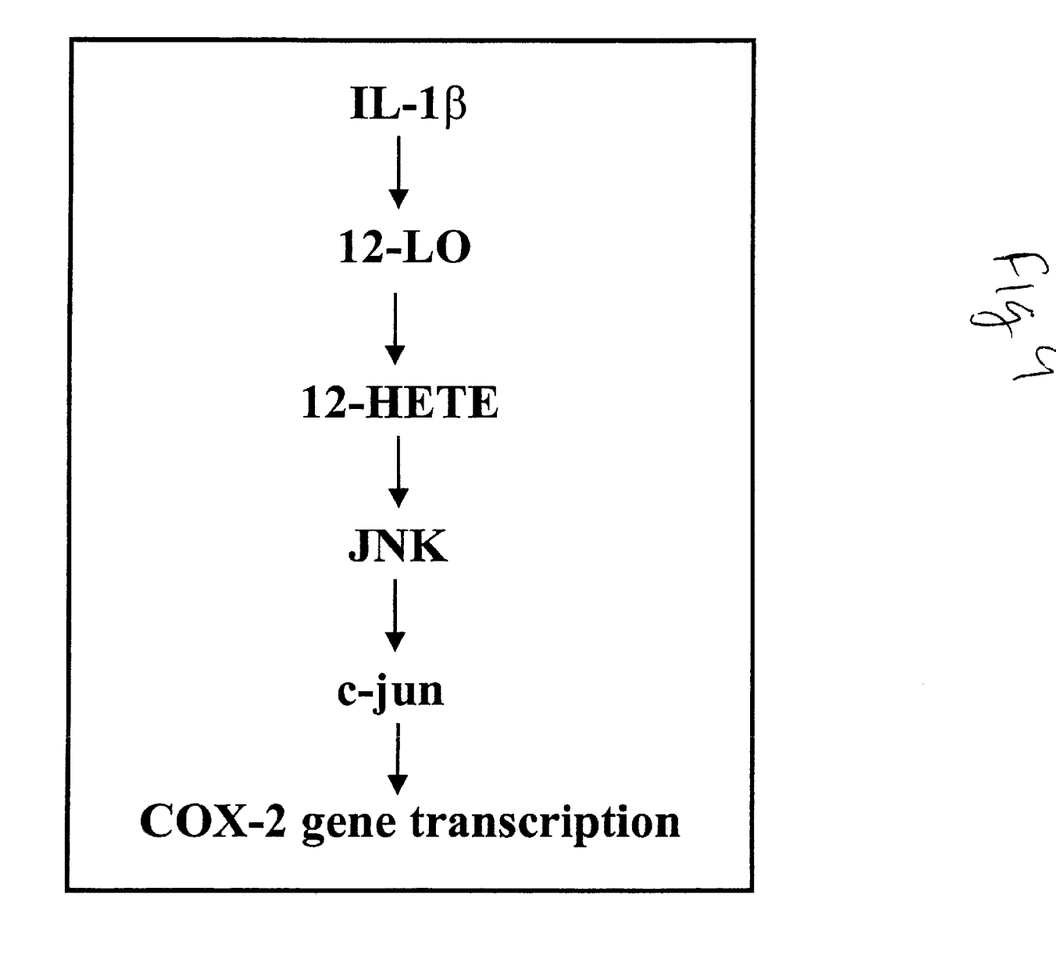
FIG. 9: Schematic diagram depicting signaling cascade leading from IL-1 β induced 12-LO activation to COX-2 gene transcription.

It has previously been published that 12-HETE, the major 12-LO end product, induces JNK in RIN m5F cells [28]. Furthermore, Herschmann and colleagues demonstrated that v-src induces COX-2 gene transcription by activating JNK and c-jun [29]. These studies demonstrate that c-jun may activate COX-2 gene transcription by binding to the cAMP response element (CRE) in the COX-2 promoter. In the present study it is demonstrated that 12-HETE acts as a specific upstream agent in activating COX-2 gene transcription. As seen in FIG. 9, a schematic signaling pathway is depicted that identifies key elements in the pathway leading from cytokine-stimulation to COX-2 gene activation in pancreatic β-cells. Furthermore, since rat tissue does not contain the putative CRE in the COX-2 promoter, it is likely that 12-HETE regulates COX-2 gene transcription through a novel promoter sequence.

Of particular interest in the present study is that 12-LO knockout mice demonstrated a decrease in basal PGE2 production compared to C57BL/6 mice. One interpretation of this finding is that 12-HETE is necessary for basal cyclooxygenase activity as well as stimulated COX-2 activity. Since both C57BL/6 islets and 12-LO KO islets presumably possess functional COX-1 enzymes it is possible that 12-HETE may regulate PGE2 production at the post-translational level, similar to NO.

The present invention offers a very advantageous means of treating inflammation by inhibition COX-2 at the transcriptional level. Previously-known COX-2 inhibitors worked at the enzyme level, by blocking COX-2 activity directly or indirectly. The natural response of the body is to compensate for loss of COX-2 activity through a biofeedback loop, that increases enzyme production. This often leads to a "rebound effect" when treatment is withdrawn. The methods of the present invention provide all of the benefits of therapeutic COX-2 inhibition, without the danger of a rebound effect, because the inhibition occurs directly at the gene level, preventing production of the enzyme.

Caffeic acid derivatives administered in accordance with the present invention can be administered, together with one or more suitable carriers or excipients, by any of several traditional routes of pharmaceutical administration, including orally, topically or by injection. The method can be readily practiced with doses of caffeic acid derivatives ranging from about 0.5 mg/kg to about 25 mg/kg [37],and preferably at about 10 mg/kg.

Examples of caffeic acid derivatives suitable for use in the present invention are cinnamamyl-3,4-dihydroxy-a-cyanocinnamate (CDC), 5,6,7-trihydroxy-2-phenyl-4H-1-benzopyran-4-one (baicalein), and the compounds listed in Table I (which have been shown to preferentially inhibit 12-LO by Cho, et al. [34]).

TABLE I

Caffeic acid derivatives

| Mol. formula | R | mol. wt. |
|---|---|---|
| $C_{12}H_{11}NO_4$ 233.23 | $C_2H_5$ | 233.23 |
| $C_{18}H_{15}NO_4$ 309.32 | $CH_2CH_2$—phenyl | 309.32 |
| $C_{19}H_{17}NO_4$ 323.35 | $CH_2CH_2CH_2$—phenyl | 323.35 |
| $C_{19}H_{19}NO_4$ 325.37 | $CH_2CH_2CH_2CH_2$—phenyl | 325.37 |
| $C_{19}H_{17}NO_5$ 339.35 | $CH_2CH_2$—(2-methoxyphenyl) | 339.35 |
| $C_{16}H_{13}NOS$ 315.35 | $CH_2CH_2$—thienyl | 315.35 |
| $C_{19}H_{15}NO_4$ 321.33 | $CH_2CH=CH$—phenyl | 321.33 |
| $C_{18}H_{16}N_2O_4$ 324.34 | $CH_2CH_2CH_2$—pyridyl | 324.34 |
| $C_{21}H_{25}N_3O_4$ 383.45 | $(CH_2)_8$—N-piperazinyl | 383.45 |

Cho, et al., J. Med. Chem., 34: 1505–08 (1991)

The following Examples are intended to illustrate the present invention, and in no way to limits its scope, which is defined by the claims. The following materials were used in the experiments set forth in the Examples:

RPMI-1640 medium was purchased from Life Technologies, Inc. (Grand Island, N.Y.). BCA reagent assay kit was from Pierce Chemical Co. (Rockford, Ill.). PGE2 RIA was purchased from P.E. Biosystems (Foster City, Calif.). Collagenase Type Xl was obtained from Sigma Chemical Company (St. Louis, Mo.) and used for islet isolation. IL-1 D was purchased from R & D Systems (Minneapolis, Minn.). CDC, 12-S-HETE, and 15-S-HETE were obtained from Biomol Research Lab, Inc. (Plymouth Meeting, Pa.). COX-2 antibody was purchased from Cayman Chemical Co (Ann Arbor, Mich.). Horseradish peroxidase conjugated anti-goat IgG was obtained from Santa Cruz Biotechnology (Santa Cruz, Calif.). COX-1 and COX-2 cDNA probes were purchased from Torrey Pines Biolabs, Inc. (San Diego, Calif.). 12-LO KO mice were a generous gift from Dr. Colin D. Funk, Center for Experimental Therapeutics, University of Pennsylvania, Pa. Porcine pancreatic islets were a generous gift from Neocrin Company (Irvine, Calif.).

EXAMPLE 1

Cell Culturing

RIN m5F cells were cultured to near confluence in RPMi-1640 medium (Life Technologies, Inc., Grand Island, N.Y.) plus 10% FCS plus 1% HEPES and penicillin/streptomycin. Prior to addition of IL-1β the cells were depleted in RPMI-1640 medium plus 0.2% BSA for 24 hours. The cells were gently washed in PBS and depletion medium was added back. At this time CDC (Biomol Research Lab, Inc., Plymouth Meeting, PA) (1–10 μM) was added in certain experiments 60 minutes prior to IL-1β addition. 12-HETE (1–100 nM) and 15-HETE (1–100 nM) (Biomol Research Lab, Inc., Plymouth Meeting, Pa.) were added to certain experiments in 0.1% ethanol. The cells were cultured for an additional 24 hours at which time medium was collected for PGE2 assay. For mRNA experiments, total RNA was extracted from RIN m5F cells 3 hours after the addition of IL-1 β, 12-HETE, or 15-HETE. 12HETE and 15-HETE were stored at –70 C. in the dark and added to cell culture dishes in the dark. Control experiments included the addition of 0.1% ethanol alone to RIN m5F cell cultures.

EXAMPLE 2

COX-2 Protein Expression in Pancreatic β-cells and Islets

We previously demonstrated that islets purified from 12-LO knockout mice are resistant to cytokine-induced inhibition of glucose stimulated insulin secretion compared to control mice [11]. This Example investigates the mechanism(s) of this resistance. RIN m5F cells, cultured as set forth in Example 1, were stimulated with IL-1β and 12-HETE and total protein extracts were used for Western immunoblotting with an anti-COX-2 antibody.

Figure 1:
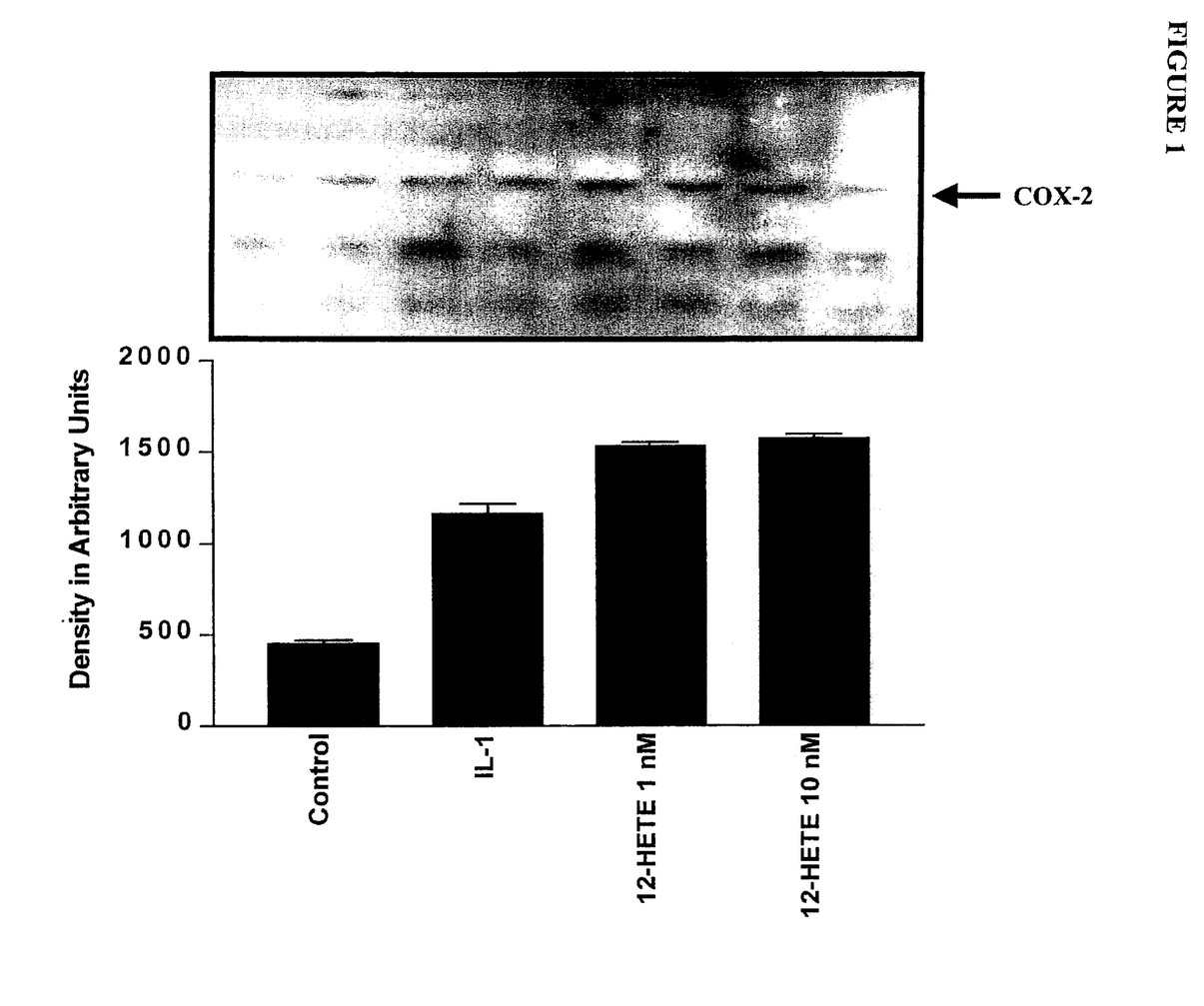

The RIN m5F cells (~300 per blot) were lysed in a 1% Triton-0.1% SDS buffer in normal saline (pH 7.4) with 10 mM HEPES plus 1 mM EDTA and standard protease inhibitors. Cell lysates were centrifuged at 14,000×9 for 10 minutes and a modified BCA protein assay was performed. Protein aliquots (50 μg per sample) were treated with Laemmeli sample buffer and then heated to 100° C. for 5 minutes. Proteins were separated on 10% SDS-PAGE and transferred to polyvinylidene difluoride membranes (Immobilon-P) in 10 mM CAPS buffer, 10% methanol at pH 11. The immunoblots were blocked overnight in 5% nonfat dried milk in Tris buffer containing 0.1% Tween-20. The blots were incubated for 2 hours at room temperature with anti COX-2 antibodies (Cayman Chemical Co., Ann Arbor, Mich.) diluted 1:2000 in the same Tris buffer without nonfat dried milk. The blots were washed and then incubated with horseradish peroxidase conjugated secondary antibodies at 1:2000 dilution. The protein bands were visualized with enhanced chemiluminescence reagents using X-AR film. As seen in FIG. 1, IL-1β (0.3 ng/ml) induced a 2.5 fold increase in COX-2 protein while 12-HETE (1–10 nM) induced a 3-fold increase.

Figure 2:
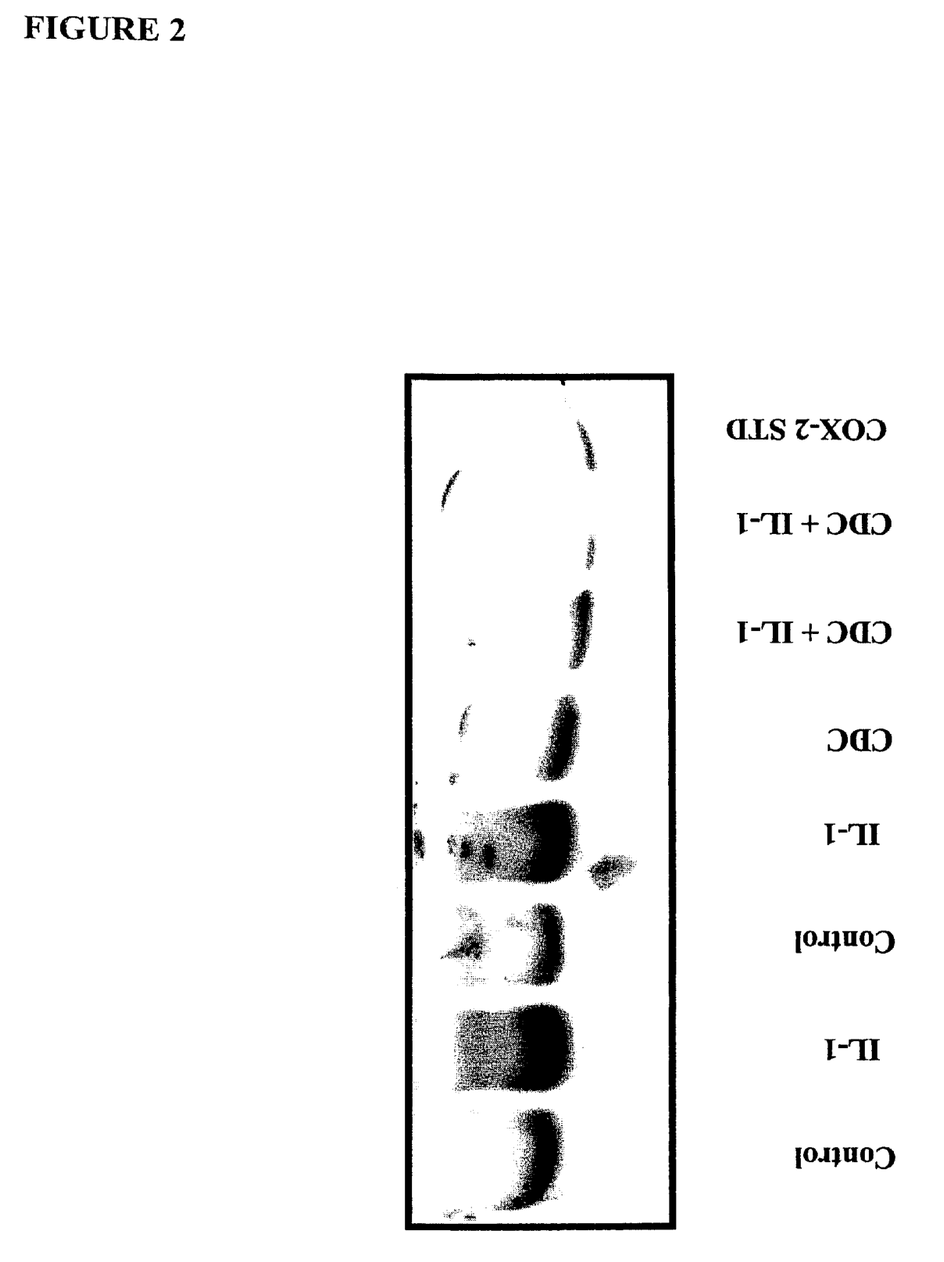

Next, Western immunoblots were performed on protein extracts from porcine islets treated in a similar fashion with IL-1β and lysed as set forth about for RIN m5F cells. Because of the concern that 12-HETE would not permeate the islet mass, the 12-LO inhibitor CDC (1 μM) was used instead with or without the addition of IL-1β, in order to determine the role of the 12-LO pathway on COX-2 protein expression. FIG. 2 demonstrates that IL-1β increased COX-2 protein 3-fold while the addition of CDC completely eliminated this response.

EXAMPLE 3

COX-2 Gene Transcription and PGE2 Production

RIN m5F cells were cultured as set forth in Example 1, in the presence or absence of IL-1β (0.3 ng/ml), 12-S-HETE (1–100 nM), or 15-S-HETE (1–100 nM) for 4 hours. Total RNA was extracted and semiquantitative RT-PCR was performed using COX-2 specific primers.

Total RNA was extracted from RIN m5F cells with RNA STAT-60 (Tel-Test, Inc., Friendswood, Tex.). RNA (1 μg) was diluted in 12.5 μl DEPC-H20 and reverse transcribed with the 1$^{st}$-Strand™ cDNA Synthesis Kit (CLONTECH laboratories, Inc., Palo Alto, Calif.), using oligo dT primers, recombinant RNase inhibitor, and MMLV reverse transcriptase to generate template cDNA for PCR amplification. Each PCR reaction was done on RNA from one 100 mm culture dish for the stated experimental conditions. Twenty picomoles of each primer (shown below) was mixed with 1 unit of Taq gold polymerase (Perkin Elmer, Inc.) in 50 μl final volume. Samples were amplified with an initial 45 second denaturation step at 94° C. followed by 25 cycles of 45 seconds at 60° C., and 25 cycles of 2 minutes at 72° C.. The last cycle was extended for an additional 7 minutes at 72° C. PCR cycling was done with a Gene Amp PCR System 2400 (Perkin Elmer/Cetus Corp., Norwalk, Conn.). DNA primers were synthesized in the DNA/RNA Core Chemistry Laboratory at City of Hope National Medical Center. The sequences of the primers are shown below.

Primers rat COX-1 sense CTG GCC GGA TTG GTG GGG GTA G antisense GTA CTC TGG GGA ACA GAT GGG rat COX-2 sense GCA AAT CCT TGC TGT TCC TCC AAT C antisense GGA GAA GGC TTC CCA GCT TTT G GAPDH sense ACG GCA AAT TCA ACG GCA CAG TCA A antisense TGG GGG CAT CGG CAG MG G PCR products were analyzed by electrophoresis with 1.8% agarose gel. The DNA was transferred to nylon membranes and hybridized sequentially to $^{32}$P-labeled probes for COX-1, COX-2, and GAPDH using a random Primed DNA labeling kit (Boehringer Mannheim). GAPDH was used as an internal control. Hybridization and autoradiography were performed according to previously published methods[14].

Figure 3:
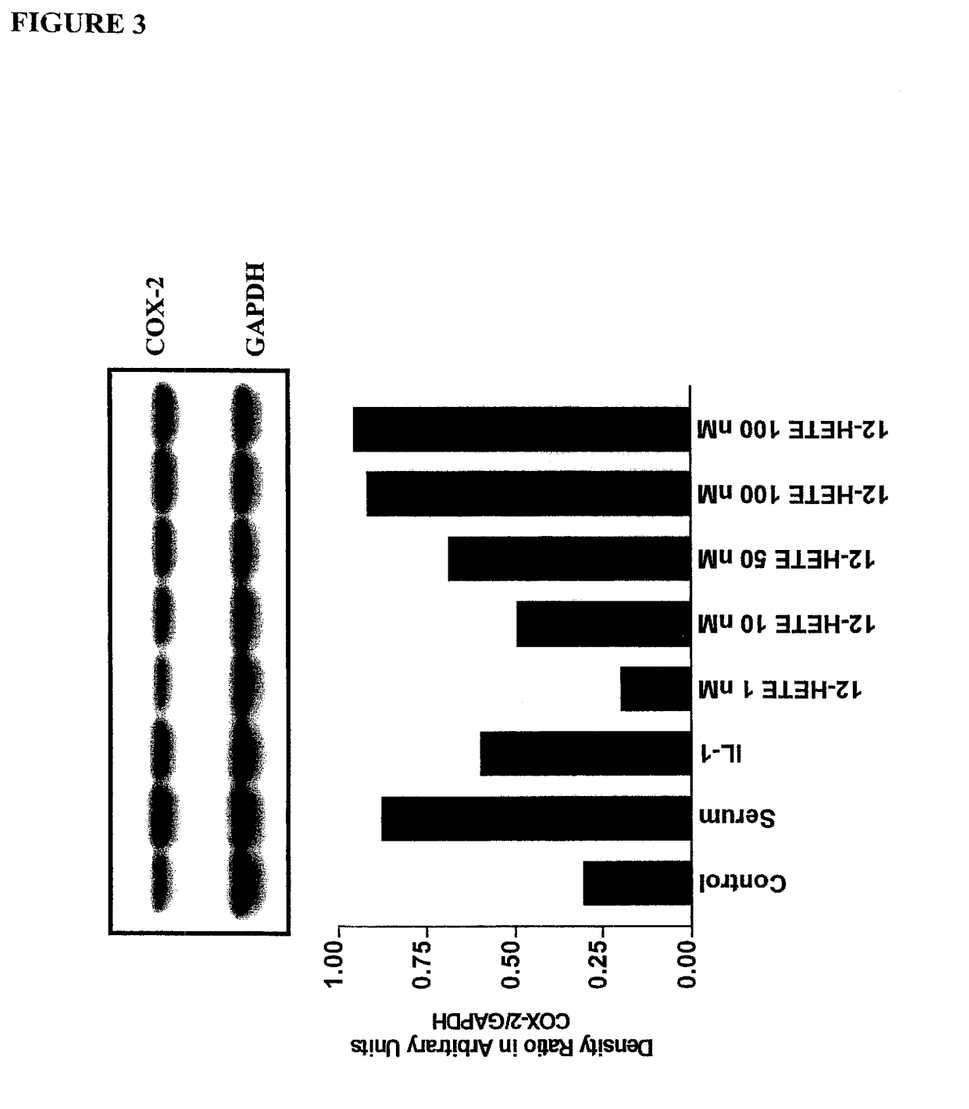
FIG. 3: Semi-quantitative RT-PCR analysis of serum, IL-1 $\beta$, and 12-HETE induced COX-2 gene expression.
Figure 4:
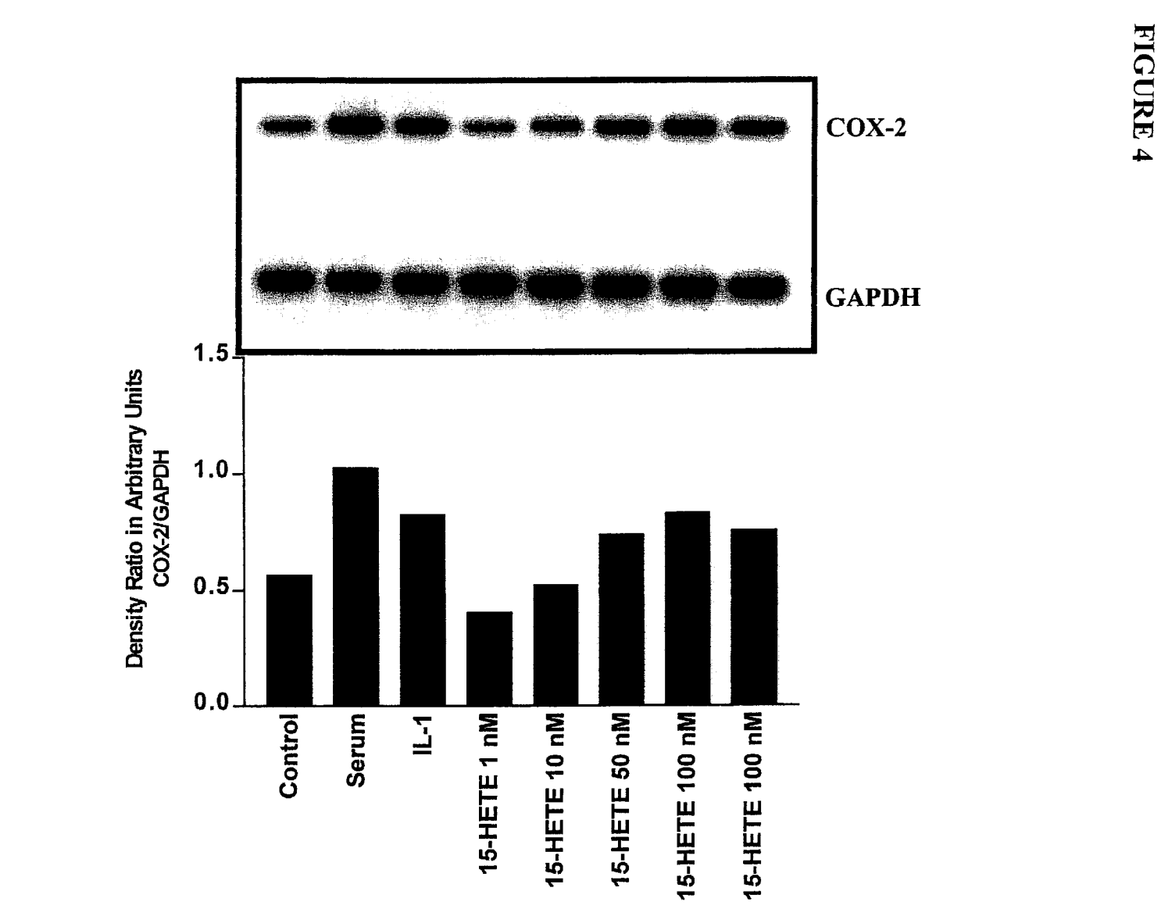
FIG. 4: Semi-quantitative RT-PCR analysis of serum, IL-1 $\beta$, and 15-HETE induced COX-2 gene expression.
Figure 5:
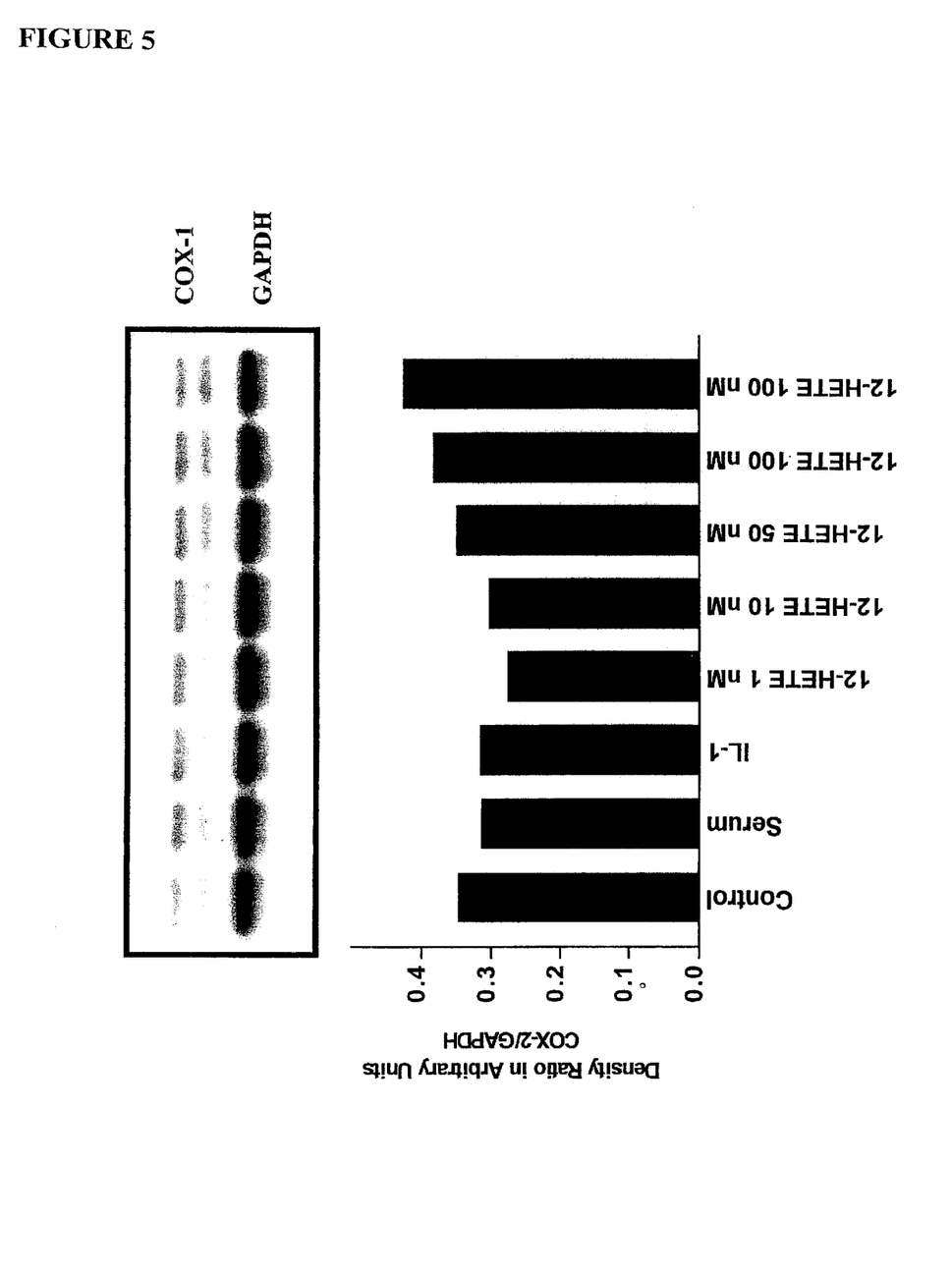
FIG. 5: Semi-quantitative RT-PCR analysis of serum, IL-1 $\beta$, and 12-HETE induced COX-1 gene expression. No appreciable difference in COX-1 mRNA expression is noted.

COX-2 mRNA was hybridized with a COX-2 probe. IL-1β induced a 2-fold increase in COX-2 mRNA as seen in FIG. 3. 12-HETE and 15-HETE induced a 3-fold and 1.5-fold increase in COX-2 mRNA, respectively (FIG. 3 and FIG. 4). The biological significance of the difference in mRNA induction by 12- and 15-HETE is further illustrated by the fact that 12-HETE stimulated a 10-fold greater increase in PGE2 than 15-HETE (see below). Then, a COX-1 specific oligonucleotide probe was used to measure COX-1 mRNA levels in the same experiments. As seen in FIG. 5, neither IL-1β,nor 12-HETE stimulated COX1 gene transcription.

In addition, PGE2 production was measured under the same conditions, but over a 24 hour period. COX-2 activity was determined by measuring the accumulation of PGE2 in the conditioned media. Cells were cultured in 24 well plates for 24 hours and subject to the experimental conditions described above. PGE2 was measured in conditioned medium using a commercial RIA kit. Statistical analysis of PGE2 levels was performed using the Student's t-test with GraphPad Prism™ software (GraphPad Software, Inc, San Diego, Calif.).

Figure 6:
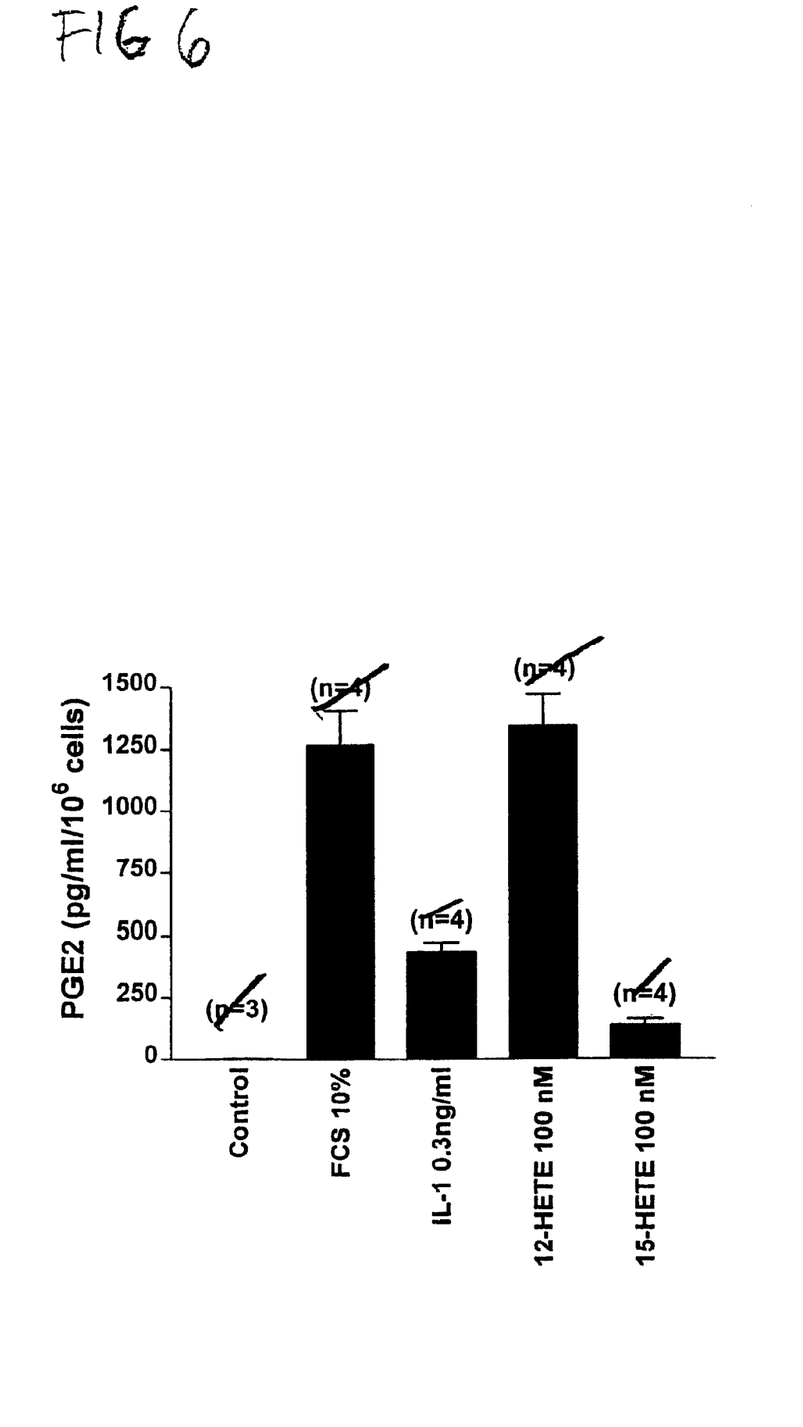
Figure 7:
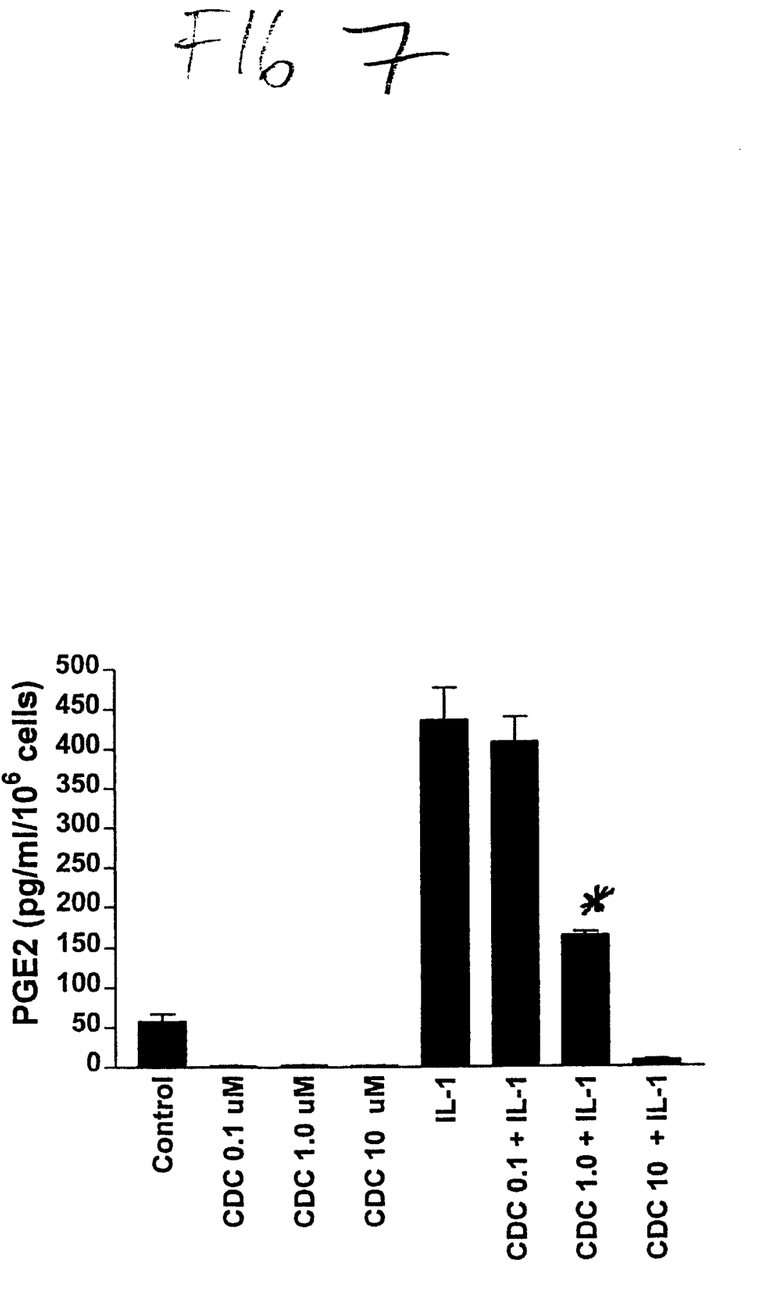
FIG. 7: CDC inhibits IL-1 β stimulated PGE2 production in RIN m5F cells. Preferential lipoxygenase pathway inhibitor CDC (luM) induced a statistically significant decrease in IL-1β induced PGE2 production as shown (*p<.01). Shown are four separate experiments for each condition.

IL-1β increased PGE2 production from virtually undetectable levels (~5 pg/ml) to ~500 pg/ml, while 12-HETE increased PGE2 production to ~1250 pg/ml. In contrast, 15-HETE induced relatively little PGE2, ~125 pg/ml (FIG. 6). CDC caused a statistically significant inhibition of IL-1β induced PGE2 production at 1 μM (388+27 pg/ml versus 169+5 pg/ml; p<.01) and this inhibition was dose-dependent (FIG. 7). It should be noted that 1 μM CDC has a relative specificity for 12-LO since the IC50 for 12-, 15-, and 5-lipoxygenase is 0.063 μM, 1.89 μM, and 3.33 μM, respectively (Biomol Research Catalogue, Sixth Edition, p. 161).

EXAMPLE 4

Islets from 12-LO Knockout Mice do not Generate PGE2

Generation of 12-LO knockout has been previously described [13]. All animal studies were performed in accordance with guidelines set forth by the Research Animal Care Committee of City of Hope National Medical Center. Islet isolation and culturing techniques have been detailed previously [14]. Briefly, mouse pancreas was removed, minced, and poured into a siliconized 25 ml Ehrlenmeyer flask with Type Xl collagenase solution (Sigma Chemical Co, St. Louis, Mo.). The pancreatic digest was incubated in a shaker-type water bath at 37 C. for 6–10 minutes. The digest was centrifuged, poured into a black back petri dish, and islets were picked by hand under a microscope. The islets were aliquoted into sterile 6-well plates (Sarstedt, Newton, N.C.) and cultured in RPMI 1640 medium containing 11 mM glucose and supplemented with 10% FCS and 1% HEPES. Typically, we isolate ~75–100 islets per mouse. For PGE2 experiments, 100 islets per well in 300 μl RPMI medium were cultured overnight prior to additions. The following morning the medium was changed to RPMI 1640 medium plus 0.2% BSA and the islets were allowed to equilibrate for one hour. Then, IL-1β (R & D Systems, Minneapolis, Minn.) was added to the appropriate experiments. All islet experiments were run in triplicate and repeated three times for reproducibility.

Isolated islets (100 per experiment) were brought to culture and incubated overnight as described. After approximately 18 hours IL-1β was added to the medium and the islets were incubated for an additional 24 hours. PGE2 production was measured as set forth in Example 3.

Figure 8:
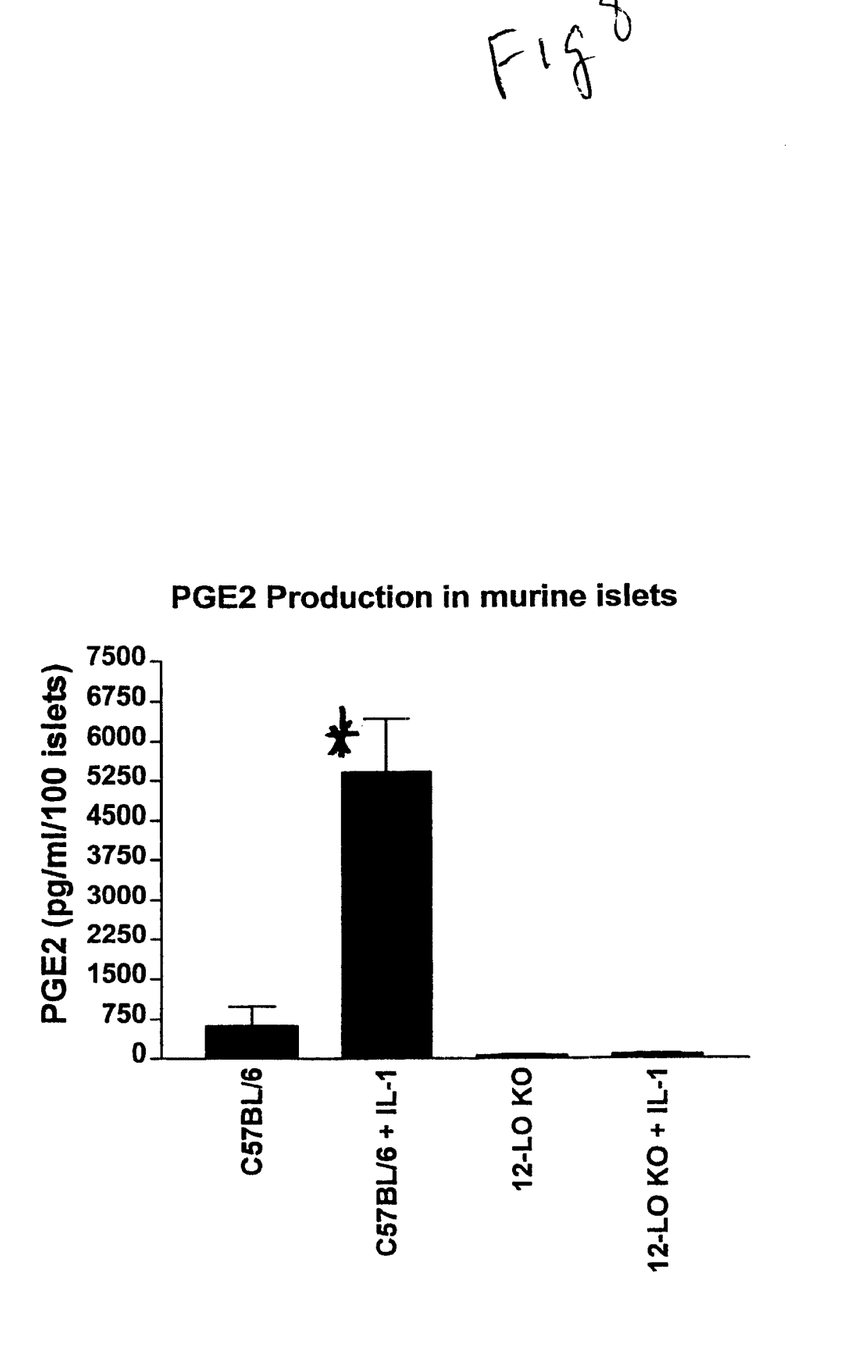
FIG. 8: PGE2 production in islets from 12-LO knockout mice and C57BL/6 mice. 12-LO knockout mice show no appreciable PGE2 production upon stimulation with IL-1 β. In marked contrast, C57BL/6 mice show 7-fold increase in PGE2 production with IL-1β stimulation (*p<.01). Shown are 3–4 separate experiments for each condition.

As seen in FIG. 8, islets from C57BU/6 mice generated 801+445 pg/ml PGE2 in the non-stimulated state. While islets stimulated with IL-1β generated 5405+1012 pg/ml PGE2, a 7-fold increase (p=.01). In marked contrast, islets isolated from 12-LO knockout mice generated 57+13 pg/ml PGE2, while islets stimulated with IL-1β generated only 78+15 pg/ml PGE2 (p=.33).

References

1. Barrios-Rodiles, M. and K. Chadee, Novel regulation of cyclooxygenase-2 expression and prostaglandin E2 production by IFN-yin human macrophages. The Journal of Immunology, 1998. 161:2441 –2448.
2. Fu, J.-Y., et al., The induction and suppression of prostaglandin H2 synthase (cyclooxygenase) in human monocytes. The Journal of Biological Chemistry, 1990. 265(28): 16737–16740.
3. Caggiano, A. O. and R. P. Kraig, Prostaglandin E receptor subtypes in cultured rat microglia and their role in reducing lipopolysaccharide-induced interleukin-1β production. Journal of Neurochemistry, 1999. 72:565–575.
4. Kujubu, D. A., et al., TIS10, a phorbol ester tumor promoter-inducible mRNA from Swiss 3T3 cells, encodes a novel prostaglandin synthase/cyclooxygenase homologue. The Journal of Biological Chemistry, 1991. 266(20):12866–12872.
5. Kujubu, D. A., et al., Expression of the protein product of the prostaglandin synthase 2/TIS10 gene in mitogen-stimulated Swiss 3T3 cells. The Journal of Biological Chemistry, 1993. 268(8):5425–5430.
6. Barnett, J., et al., Purification, characterization and selective inhibition of human prostaglandin G/H synthase 1 and 2 expressed in the baculovirus system. Biochimica et Biophysica Acta,1994.1209:130–139.
7. Robertson, R. P., Dominance of cyclooxygenase-2 in the regulation of pancreatic islet prostaglandin synthesis. Diabetes,1998. 47:1379–1383.
8. Metz, S. A., R. P. Robertson, and W. Y. Fujimoto, Inhibition of prostaglandin Synthesis augments glucose-induced insulin secretion in cultured pancreas. Diabetes, 1981. 30(7):551 –557.
9. Robertson, R. P., et al., Receptor-mediated adenylate cyclase-coupled mechanism for PGE2 inhibition of insulin secretion in HIT cells. Diabetes, 1987. 36(9):1047–1053.
10. Shannon, V. R., et al. Selective expression of an arachidonate 12-lipoxygenase by pancreatic islet β-cells. American Journal of Physiology, 1992. 263:E828–836.
11. Bleich, D., et al., Resistance to type 1 diabetes induction in 12-lipoxygenase knockout mice. The Journal of Clinical Investigation, 1999.103:1431–1436.
12. Barry, O. P., et al., Arachidonic acid in platelet microparticles up-regulates cyclooxygenase-2-dependent prostaglandin formation via a protein kinase C/mitogen activated protein kinase-dependent pathway. The Journal of Biological Chemistry, 1999. 274(11):7545–7556.
24. Corbett, J. A., et al., IL-1β induces the coexpression of both nitric oxide synthase and cyclooxygenase by Islets of Langerhans: Activation of cyclooxygenase by nitric oxide. Biochemistry, 1993. 32:13767–13770.
25. Ma, Z., et al., Interleukin-1 enhances pancreatic islet arachidonic acid 12-lipoxygenase product generation by increasing substrate availability through a nitric oxide-dependent mechanism. The Journal of Biological Chemistry, 1996. 271(2):1029–1042.
26. Turk, J., et al., Arachidonic acid metabolism and insulin secretion by isolated human pancreatic islets. Diabetes, 1988. 37:992–996.
27. Metz, S. Exogenous arachidonic acid promotes insulin release from intact or permeabilized rat islets by dual mechanisms. Diabetes, 1988. 37:1453–1469.
28. Bleich, D., et al., The stress-activated c-jun protein kinase (JNKJ is stimulated by lipoxygenase pathway product 12-HETE in RIN m5F cells. Biochemical and Biophysical Research Communications, 1997. 230:448–451.

29. Xie, W. and H. R. Herschman, v-src induces prostaglandin synthase 2 gene expression by activation of the c-jun N-terminal kinase and the c-jun transcription factor. The Journal of Biological Chemistry, 1995. 270(46):27622–27628.
30. Callejas, N. A., et al., Inhibition of prostaglandin synthesis up-regulates cyclooxygenase-2 induced by lipopolysaccharide and peroxisomal proliferators, J. Pharm. Exp. Ther., 1999. 288:1235–1241.
31. Chan, C.-C., et al., Rofecoxib [Vioxx, MK-0966; 4-(4'-methylsulfonylphenyl)-3-phenyl-2-(5H)-furanone]: a potent and orally active cyclooxygenase-2 inhibitor. Pharmacological and biochemical profiles, J. Pharm. Exp. Ther., 1999. 290:551–560.
32. Gierse, J. K., et al., Kinetic basis for selective inhibition of cyclo-oxygenases, Biochem J., 1999. 339:607–614.
33. Marnett, L. J., et al., Arachidonic acid oxidation by COX-1 and COX-2, J. Biol. Chem., 1999. 274:22903–22906.
34. Cho, H., et al., Novel caffeic acid derivatives: extremely potent inhibitors of 12-lipoxygenase, J. Med. Chem., 1991. 34:1503–1505.
35. Michaluart, P., Masferrer, J. L., Carothers, A. M., Subbaramaiah, K., Zweifel, B. S., Koboldt, C., Mestre, J. R., Grunberger, D., Sacks, P. G., Tanabe, T., A. J. Dannenberg, Inhibitory effects of caffeic acid phenethyl ester on the activity and expression of cyclooxygenase-2 in human oral epithelial cells and in a rat model of inflammation, Cancer Research, 1999. 59:2347–2352.
36. Kirchner, T., Argentieri, D. C. Barbone, A. G., Singer, M., Steber, M., Ansell, J., Beers, S. A., Wachter, M. P., Wu, W., Malloy, E., Stewart, A., and D. M. Ritchie, Evaluation of the antiinflammatory activity of a dual cyclooxygenase-2 selective/5-lipoxygenase inhibitor, RWJ 63556, in a canine model of inflammation, Journal of Pharmacology and Experimental Therapeutics, 1997. 282:1094–1101.
37. Uang Y. S., Hsu, K. Y., A dose-dependent pharmacokinetic study on caffeic acid in rabbits after intravenous administration, Biopharm. Drug Dispos., 1997. 8:727–736.

We claim:

1. A method of treating inflammation comprising administering to a subject in need thereof an amount of a caffeic acid derivative sufficient to inhibit selectively the transcription of COX-2.

2. The method of claim 1 wherein the caffeic acid derivative is a cyanocinnamate.

3. The method of claim 2 wherein the cyanocinnamate is cinnamamyl-3,4-dihydroxy-α-cyanocinnamate.

4. The method of claim 1 wherein the caffeic acid derivative is in a dose of about 0.5 mg/kg to about 25 mg/kg.

5. The method of claim 4 wherein the caffeic acid derivative is in a dose of about 10 mg/kg.

* * * * *